United States Patent
Randall et al.

(12)

(10) Patent No.: US 6,265,636 B1
(45) Date of Patent: Jul. 24, 2001

(54) PYRUVATE DEHYDROGENASE KINASE POLYNUCLEOTIDES, POLYPEPTIDES AND USES THEREOF

(75) Inventors: Douglas D. Randall; Jay J. Thelen, both of Columbia, MO (US); Jan A. Miernyk, Peoria, IL (US); Michael G. Muszynski, Des Moines; Vincent J. H. Sewalt, West Des Moines, both of IA (US)

(73) Assignees: Pioneer Hi-Bred International, Inc., Des Moines, IA (US); University of Missouri, Columbia, MO (US)

( * ) Notice: Subject to any disclaimer, the term of this patent is extended or adjusted under 35 U.S.C. 154(b) by 0 days.

(21) Appl. No.: 09/333,423

(22) Filed: Jun. 15, 1999

Related U.S. Application Data

(60) Provisional application No. 60/089,998, filed on Jun. 19, 1998.

(51) Int. Cl.[7] ............................. C12N 5/04; C12N 15/29; C12N 15/82; A01H 5/00; A01H 5/10
(52) U.S. Cl. ..................... 800/284; 800/278; 800/286; 800/293; 800/298; 800/306; 800/312; 800/314; 800/320.1; 800/320.2; 800/320.3; 800/322; 800/281; 800/320; 435/69.1; 435/419; 435/468; 435/320.1; 536/23.1; 536/23.2; 536/23.6; 536/24.1; 536/24.5
(58) Field of Search ..................................... 800/284, 298, 800/293, 286, 320, 320.1, 320.2, 320.3; 435/69.1, 468, 419, 320.1; 536/23.1, 23.2, 23.6, 24.5

(56) References Cited

PUBLICATIONS

Chevalier et al. Plant Molecular Biology, vol. 28, pp. 473–485, 1995.*
Yamamoto et al. Aceession No. C224239, Desposited, Aug. 1997.*
Popov et al. The Journal of Biological Chemistry, vol. 269 (47), pp. 29720–29724, 1994.*
Bird et al. Biotechnology and Gen. Eng. Review, vol. 9, pp. 207–227, Dec. 1991.*
Sandler et al. Plant Mol. Biol. vol. 11, pp. 301–310, 1988.*
Smith et al. Nature, vol. 334, pp. 724–726, Aug. 1988.*
Kossmen et al. progress in Biotech–10, proceed. Int. Cont pp. 271–278, Apr. 1995.*

* cited by examiner

Primary Examiner—David T. Fox
Assistant Examiner—Medina A. Ibrahim
(74) Attorney, Agent, or Firm—Pioneer Hi-Bred International, Inc.

(57) ABSTRACT

The invention provides methods and compositions relating to altering carbohydrate metabolism and/or composition of plants. The invention provides isolated nucleic acids and their encoded proteins, expression cassettes, host cells, transgenic plants, and antibody compositions.

52 Claims, No Drawings

US 6,265,636 B1

PYRUVATE DEHYDROGENASE KINASE POLYNUCLEOTIDES, POLYPEPTIDES AND USES THEREOF

This application claims priority under 35 U.S.C. 119(e) to U.S. Provisional Patent Application 60/089,998, filed Jun. 19, 1998, which is hereby incorporated by reference.

TECHNICAL FIELD

The present invention relates generally to plant molecular biology. More specifically, it relates to nucleic acids and methods for modulating their expression in plants.

BACKGROUND OF THE INVENTION

The mitochondrial pyruvate dehydrogenase complex (mtPDC) catalyzes the decarboxylation of pyruvate yielding acetyl-CoA and NADH which are precursors of the Krebs cycle and oxidative phosphorylation. The mtPDC provides acetyl-CoA for the citrate synthase and acetyl-CoA hydrolase reactions and NADH for the electron transport system.

Pyruvate dehydrogenase complex (PDC) contains three primary component enzymes, pyruvate dehydrogenase (PDH, E1), dihydrolipoamide transacetylase (E2) and dihydrolipoamide dehydrogenase (E3).

The mtPDC provides a site for regulation due to its strategic metabolic location and the irreversible nature of the reaction. All PDCs exhibit product inhibition by acetyl-CoA and NADH. For mtPDCs, but not plastidial PDCs, reversible phosphorylation of the alpha subunit of E1 provides and "off-on" switch for mtPDC activity.

Reversible phosphorylation of PDC is catalyzed by two regulatory enzymes, PDH kinase (PDK) and P-PDH phosphatase. Both of these regulatory enzymes are specific for PDH.

SUMMARY OF THE INVENTION

It is the object of the present invention to provide nucleic acids and proteins relating to carbohydrate metabolism.

It is another object of the present invention to provide antigenic fragments of the proteins of the present invention.

It is another object of the present invention to provide transgenic plants comprising the nucleic acids of the present invention.

It is another object of the present invention to provide methods for modulating, in a transgenic plant, the expression of the nucleic acids of the present invention.

It is another object of the present invention to provide methods for manipulating cell metabolism in plants.

According to the present invention an isolated nucleic acid is provided comprising a member selected from the group consisting of a) a polynucleotide that encodes a polypeptide of SEQ ID NO: 2 or 4;

b) a polynucleotide amplified from a *Zea mays* nucleic acid library using the primers of SEQ ID NOS: 5 and 6;

c) a polynucleotide comprising at least 25 contiguous bases of SEQ ID NOS: 1 or 3;

d) a polynucleotide having at least 60% sequence identity to SEQ ID NOS: 1 or 3, wherein the % sequence identity is based on the entire sequence and is determined by BLAST 2.0 under default parameters;

e) a polynucleotide comprising at least 25 nucleotides in length which hybridizes under low stringency conditions to a polynucleotide having the sequence set forth in SEQ ID NO: 1 or 3, wherein the conditions include hybridization with a buffer solution of 30% formamide, 1 M NaCl, 1% SDS at 37° C. and a wash in 2×SSC at 50° C.;

f) a polynucleotide complementary to a polynucleotide of (a) through (e).

In another aspect, the polynucleotide comprises a sequence selected from the group consisting of SEQ ID NOS: 1 and 3.

In another aspect, the present invention relates to an isolated protein comprising a member selected from the group consisting of:

a) a polypeptide comprising at least 10 contiguous amino acids of SEQ ID NO: 2 or 4;

b) a polypeptide comprising at least 60% sequence identity to SEQ ID NO: 2 and 4, wherein the % sequence identity is based on the entire sequence and is determined by BLAST 2.0 using default parameters;

c) a polypeptide encoded by a nucleic acid of claim 1; and d) a polypeptide characterized by SEQ ID NO: 2 or 4.

In another aspect, the present invention relates to expression cassettes, comprising a nucleic acid as described, supra, operably linked to a promoter.

In another aspect, the nucleic acid is operably linked in antisense orientation to the promoter.

In another aspect, the present invention is directed to a host cell transfected with the expression cassette.

In another aspect, the present invention is directed to a method of modulating the level of PDK protein in a plant, comprising:

a) stably transforming a plant cell with a PDK polynucleotide operably linked to a promoter, wherein the polynucleotide is in sense or antisense orientation;

b) growing the plant cell under plant growing conditions to produce a regenerated plant; capable expressing the polynucleotide for a time sufficient to modulate PDK protein in the plant.

In yet another aspect, the present invention relates to a transgenic plant comprising an expression cassette comprising a plant promoter operably linked to any of the isolated nucleic acids of the present invention. In some embodiments, the transgenic plant is *Zea mays*. The present invention also provides transgenic seed from the transgenic plant.

In a further aspect, the present invention relates to a method of modulating expression of the genes encoding the proteins of the present invention in a plant, comprising the steps of (a) transforming a plant cell with an expression cassette comprising a polynucleotide of the present invention operably linked to a promoter; (b) growing the plant cell under plant growing conditions; and (c) inducing expression of the polynucleotide for a time sufficient to modulate expression of the genes in the plant. In some embodiments, the plant is maize. Expression of the genes encoding the proteins of the present invention can be increased or decreased relative to a non-transformed control plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledenous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or produced by non-natural, synthetic, methods, or if it is transcribed from DNA which has been altered, by non-natural, synthetic methods. The isolated nucleic acid may also be produced by the synthetic re-arrangement ("shuffling") of a part or parts of one or more allelic forms of the gene of interest. Likewise, a naturally occurring nucleic acid (e.g., a promoter) becomes isolated if it is introduced to a locus of the genome not native to that nucleic acid. Nucleic acids which are "isolated" as defined herein, are also referred to as "heterologous" nucleic acids.

Unless otherwise stated, the term "pyruvate dehydrogenase kinase nucleic acid" means a nucleic acid comprising a polynucleotide ("pyruvate dehydrogenase kinase polynucleotide") encoding a pyruvate dehydrogenase kinase polypeptide. A "pyruvate dehydrogenase kinase gene" refers to a non-heterologous genomic form of a full-length pyruvate dehydrogenase kinase polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning-A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. Preferably the plant is maize, soybean, sorghum, wheat, rice, sunflower, alfalfa, cotton, barley, millet, or Brassica. A particularly preferred plant is *Zea mays*.

As used herein, "polynucleotide" includes reference to a deoxyribopolynucleotide, ribopolynucleotide, or analogs thereof, that have the essential nature of a natural ribonucleotide in that they hybridize to nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotidesas the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins-Structure and Molecular Properties*, 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp.1–12 in *Posttranslational Covalent Modification of Proteins, B. C. Johnson, Ed., Academic Press, New York (*1983); Seifter et al., *Meth. Enzymol.* 182: 626–646 (1990) and Rattan et al., *Protein Synthesis: Posttranslational Modifications and Aging*, Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, seeds, fibers, xylem vessels, tracheids, or sclerenchyma. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "pyruvate dehydrogenase kinase polypeptide" refers to one or more amino acid sequences, in glycosylated or non-glycosylated form, involved in regulation of the pyruvate dehydrogenase complex that links glycolysis to the tricarboxylic acid cycle (alternatively: regulates pyruvate metabolism at the site entry into the tricarboxylic acid cycle). The term is also inclusive of fragments, variants, homologs, alleles or precursors (e.g., preproproteins or proproteins) thereof. A "pyruvate dehydrogenase kinase protein" comprises a pyruvate dehydrogenase kinase polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, an "expression cassette" is a nucleic acid construct, generated recombinantly or synthetically, with a series of specified nucleic acid elements which permit transcription of a particular nucleic acid in a target cell. The expression cassette can be incorporated into a plasmid, chromosome, mitochondrial DNA, plastid DNA, virus, or nucleic acid fragment. Typically, the expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to a hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York (1988), for a description of immunoassay formats and conditions that can be used to determine selective reactivity.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of an expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50,100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443–453 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST 2.0 family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

As those of ordinary skill in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides compositions and methods for modulating (i.e., increasing or decreasing) the total levels of proteins of the present invention and/or altering their ratios in plants. Thus, the present invention provides utility in such exemplary applications as control of carbohydrate metabolism. In particular, the polypeptides of the present invention can be expressed at times or in quantities which are not characteristic of non-recombinant plants.

The present invention also provides isolated nucleic acid comprising polynucleotides of sufficient length and complementarity to a pyruvate dehydrogenase kinase gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for expression of pyruvate dehydrogenase kinase polypeptides, or for use as immunogens in the preparation and/or screening of antibodies. The isolated nucleic acids of the present invention can also be employed for use in sense or antisense suppression of one or more pyruvate dehydrogenase kinase genes in a host cell, tissue, or plant. Attachment of chemical agents which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated pyruvate dehydrogenase kinase genes from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes*, 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the pyruvate dehydrogenase kinase polypeptides (e.g., preproenzyme, proenzyme, or enzymes) as disclosed herein. The present invention also provides proteins comprising at least one epitope from a pyruvate dehydrogenase kinase polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of pyruvate dehydrogenase kinase polypeptides.

The present invention provides maize pyruvate dehydrogenase kinases (PDK). These kinases control the activity of the mitochondrial pyruvate dehydrogenase complex in plants via a reversible phosphorylation event.

The mitochondrial pyruvate dehydrogenase complex has a specific pyruvate dehydrogenase kinase and phospho-pyruvate dehydrogenase phosphatase which catalyze the reversible phosphorylation of the α subunit of the pyruvate dehydrogenase component. Pyruvate dehydrogenase kinase catalyzes inactivation of pyruvate dehydrogenase complex while phospho-pyruvate dehydrogenase phosphatase reactivates pyruvate dehydrogenase complex. Consequently, the in vivo phosphorylation status of pyruvate dehydrogenase complex is determined by the net activities of these opposing enzymes and physiological effectors of plant pyruvate dehydrogenase kinases would thus regulate the phosphorylation status of pyruvate dehydrogenase complex in vivo.

Mitochondrial pyruvate dehydrogenase complexes catalyze the decarboxylation of pyruvate yielding acetyl-CoA and NADH that are precursors of the Krebs cycle and oxidative phosphorylation. The acetyl-CoA is a precursor for the citrate synthase reaction as well as the acetyl-CoA hydrolase reaction and NADH provides reducing equivalents for the electron transport system. Modulation of the maize pyruvate dehydrogenase kinases would provide a mechanism for manipulating cellular metabolism in plants.

Pyruvate dehydrogenase complexes contain three primary component enzymes, pyruvate dehydrogenase (E1), dihydrolipoamide transacetylase (E2) and dihydrolipoamide dehydrogenase (E3).

The mitochondrial pyruvate dehydrogenase complex provides a site for regulation due to its strategic metabolic location and the reversible nature of the reaction. All pyruvate dehydrogenase complexes exhibit product inhibition by acetyl-CoA and NADH. For mitochondrial pyruvate dehydrogenase complexes reversible phosphorylation of the alpha subunit of E1 provides an "off-on" switch for mitochondrial pyruvate dehydrogenase complex activity.

Reversible phosphorylation of pyruvate dehydrogenase complex is catalyzed by two regulatory enzymes, pyruvate dehydrogenase kinase and phospho-pyruvate dehydrogenase phosphatase. Both of these regulatory enzymes are specific for pyruvate dehydrogenase.

Pyruvate is involved in a number of primary metabolic processes including carbohydrate metabolism and biosynthesis of fatty acids, isoprenoids, amino acids, terpenes and steroids.

The maize cDNAs encode polypeptides with 30% overall amino acid identity to the mammalian pyruvate dehydrogenase kinase. The maize kinases have five domains with conserved signature residues. The cDNAs described in this invention are 1332 (PDK1) and 1602 (PDK2) nucleotides in length encoding polypeptides with calculated molecular weight of 38,867 and 41,327 that share 77% amino acid identity. Genomic DNA Southern analysis confirm these kinases are members of a multigene family in maize. RNA blot analysis show a 1.6 kb transcript present predominantly in leaves and a low abundance transcript of 1.3 kb present in leaves. Maize PDK expressed as a chimera with maltose binding protein is capable of phosphorylating and inactivating PDK depleted maize mtPDC. Thus the proteins encoded by these cDNA's have PDK function.

The entire open reading frames of SEQ ID NOS: 1 and 3 can be PCR amplified for bacterial expression with an N-terminal 6 histidine tag to facilitate purification by Ni-chelate chromatography. Purified recombinant PDK1 and PDK2 migrated at 44 and 25/48 kD, respectively, on SDS-PAGE. Anti-PDK1 antibodies immunoprecipitated 75% of pyruvate dehydrogenase kinase activity from a maize mitochondrial matrix extract and by immunoblot using monospecific polyclonal antibodies a single mitochondrial matrix protein was recognized at 43 kD. Analyses recognized three matrix proteins of 39, 41 and 23 kD with abundance in that order.

The isolated nucleic acids of the present invention can be used in a broad range of plant types, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, and Populus.

Nucleic Acids

The present invention provides, inter alia, isolated nucleic acids of RNA, DNA, and analogs and/or chimeras thereof, comprising a pyruvate dehydrogenase kinase polynucleotide encoding such enzymes as:

The pyruvate dehydrogenase kinase nucleic acids of the present invention comprise isolated pyruvate dehydrogenase kinase polynucleotides which, are inclusive of:

(a) a polynucleotide encoding a pyruvate dehydrogenase kinase polypeptide of SEQ ID NOS: 2 or 4 and conservatively modified and polymorphic variants thereof, including exemplary polynucleotides of SEQ ID NOS: 1 or 3;

(b) a polynucleotide which is the product of amplification from a Zea mays nucleic acid library using primer pairs from amongst the consecutive pairs from SEQ ID NOS: 5 and 6, which amplify polynucleotides having substantial identity to polynucleotides from amongst those having SEQ ID NOS: 1 and 3;

(c) a polynucleotide which selectively hybridizes to a polynucleotide of (a) or (b);

(d) a polynucleotide having at least 60% sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least 15 contiguous nucleotides from a polynucleotide of (a), (b), (c), (d), (e), or (f).

A. Polynucleotides Encoding A Protein of SEQ ID NOS: 2 or 4 or Conservatively Modified or Polymorphic Variants Thereof As indicated in (a), supra, the present invention provides isolated heterologous nucleic acids comprising a pyruvate dehydrogenase kinase polynucleotide, wherein the polynucleotide encodes a pyruvate dehydrogenase kinase polypeptide. The nucleic acid is disclosed herein in SEQ ID NOS: 1 and 3, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1 and 3, and silent variations of polynucleotides encoding a polypeptide of SEQ ID NOS: 2 and 4. The present invention further provides isolated nucleic acids comprising polynucleotides encoding conservatively modified variants of a polypeptide of SEQ ID NOS: 2 and 4. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides. Polymorphisms are frequently used to follow segregation of chromosomal regions in, for example, marker assisted selection methods for crop improvement.

Pyruvate dehydrogenase kinase is coded for by the polypeptides of SEQ ID NOS: 2 or 4 which are encoded for by the nucleic acids of SEQ ID NOS: 1 or 3 respectively.

B. Polynucleotides Amplified from a *Zea mays* Nucleic Acid Library

As indicated in (b), supra, the present invention provides isolated nucleic acids comprising pyruvate dehydrogenase kinase polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs. In preferred embodiments, the cDNA library is constructed. The polynucleotides of the present invention include those amplified using the following primer pairs:

SEQ ID NOS: 5 and 6 which yield an amplicon comprising a sequence having substantial identity to SEQ ID NO: 1 and 3.

The present invention also provides subsequences of full-length nucleic acids. Any number of subsequences can be obtained by reference to SEQ ID NOS: 1 and 3, and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38.); see also, U.S. Pat. No. 5,470,722, and *Current Protocols in Molecular Biology*, Unit 15.6, Ausubel, et al., Eds., Greene Publishing and Wiley-Interscience, New York (1995). Thus, the present invention provides pyruvate dehydrogenase kinase polynucleotides having the sequence of the pyruvate dehydrogenase kinase gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR amplification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof) of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5' end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 1 and 3, from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc., Catalog '97, p.354.

C. Polynucleotides Which Selectively Hybridize to a Polynucleotide of (A) or (B)

As indicated in (c), supra, the present invention provides isolated nucleic acids comprising pyruvate dehydrogenase kinase polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated from a *Zea mays* nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising pyruvate dehydrogenase kinase polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising pyruvate dehydrogenase kinase polynucleotides, wherein the polynucleotides encode a protein having a subsequence of contiguous amino acids from a prototype pyruvate dehydrogenase kinase polypeptide. Exemplary prototype pyruvate dehydrogenase kinase polypeptides are provided in SEQ ID NOS: 2 and 4. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as, but not limited to, a polypeptide encoded by the polynucleotide of (b), supra, or exemplary polypeptides of SEQ ID NOS: 2 and 4. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated pyruvate dehydrogenase kinase polypeptides as disclosed herein (e.g., SEQ ID NOS: 2 and 4). Molecular weight can be readily determined by SDS-PAGE under reducing conditions. Preferably, the molecular weight is within 15% of a full length pyruvate dehydrogenase kinase polypeptide, more preferably within 10% or 5%, and most preferably within 3%, 2%, or 1% of a full length pyruvate dehydrogenase kinase polypeptide of the present invention. Molecular weight determination of a protein can be conveniently performed by SDS-PAGE under denaturing conditions.

Optionally, the polynucleotides of this embodiment will encode a protein having a specific activity at least 20%, 30%, 40%, or 50% of the native, endogenous (i.e., non-isolated), full-length pyruvate dehydrogenase kinase polypeptide. Further, the proteins encoded by polynucleotides of this embodiment will optionally have a substantially similar apparent dissociation constant ($K_m$) and/or catalytic activity (i.e., the microscopic rate constant, $k_{cat}$) as the native endogenous, full-length pyruvate dehydrogenase kinase protein. Those of skill in the art will recognize that $k_{cat}/K_m$ value determines the specificity for competing substrates and is often referred to as the specificity constant. Proteins of this embodiment can have a $k_{cat}/K_m$ value at least 10% of the non-isolated full-length pyruvate dehydrogenase kinase polypeptide as determined using the substrate of that polypeptide from the pyruvate dehydrogenase kinase specific pathways, supra. Optionally, the $k_{cat}/K_m$ value will be at least 20%, 30%, 40%, 50%, and most preferably at least 60%, 70%, 80%, 90%, or 95% the $k_{cat}/K_m$ value of the non-isolated, full-length pyruvate dehydrogenase kinase polypeptide. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), supra, the present invention provides isolated nucleic acids comprising pyruvate dehydrogenase kinase polynucleotides, wherein the polynucleotides are complementary to the polynucleotides of paragraphs A–E, above. As those of skill in the art will recognize, complementary sequences base-pair throughout the entirety of their length with the polynucleotides of (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), supra, the present invention provides isolated nucleic acids comprising pyruvate dehydrogenase kinase polynucleotides, wherein the polynucleotide comprises at least 15 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, such as SEQ ID NOS: 2 and 4, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is generally a vector, adapter, or linker for cloning and/or expression of a polynucleotide of the present invention. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc., Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, strand cDNA synthesis is initiated from a poly(A)$^+$ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adapters. Ligation of the adapters will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as: Stratagene, and Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.* 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19(8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage etaL., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

The present invention further provides expression cassettes comprising a nucleic acid of the present invention. A nucleic acid sequence coding for the desired polynucleotide of the present invention, for example a cDNA or a genomic sequence encoding a full length polypeptide of the present invention, can be used to construct an expression cassette which can be introduced into the desired host cell. An expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in expression cassettes to drive expression of antisense nucleic acids to reduce, increase, or alter pyruvate dehydrogenase kinase content and/or composition in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see Kmiec, U.S. Pat. No. 5,565,350; Zarling et al., PCT/US93/03868), or isolated promoters can be introduced into a plant cell in the proper orientation and distance from a pyruvate dehydrogenase kinase gene so as to control the expression of the gene. Gene expression can be modulated under conditions suitable for plant growth so as to alter pyruvate dehydrogenase kinase content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, New York (1994); *Corn and Corn Improvement*, 3$^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; DNA probe arrays; and isolation of proteins known to be expressed with some specificity in the target tissue. Such methods are well known to those of skill in the art. Commercially available products for isolating promoters are known in the art such as the Clontech (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227, 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., Genes Dev. 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., Nature 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc.* (1987) 109:1241–1243). Meyer, R. B., et al., *J Am Chem Soc.* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc.* (1990) 112:2435–2437. Use of N4, N4-ethanocytosine as an alkylating agent to crosslink to single-stranded oligonucleotides has also been described by Webb and Matteucci, *J Am Chem Soc.* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 2 and 4. The proteins of the present invention or variants thereof can comprise any number of contiguous amino acid residues from a polypeptide of the present invention, wherein that number is selected from the group of integers consisting of from 10 to the number of residues in a full-length pyruvate dehydrogenase kinase polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 2 and 4. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in E. coli is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., Gene 22: 229–235 (1983); Mosbach, et al., Nature 302: 543–545 (1983)).

B. Expression in Eukaryotes

A variety of eukaryotic expression systems such as yeast, insect cell lines, plant and mammalian cells, are known to those of skill in the art. As explained briefly below, pyruvate dehydrogenase kinase proteins of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., Methods in Yeast Genetics, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., Gene 8: 17–24 (1979); Broach, et al., Gene 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct an expression cassette which can be introduced into the desired plant.

Isolated nucleic acid acids of the present invention can be introduced into plants according techniques known in the art. Generally, expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5824 (1985). Ballistic transformation techniques are described in Klein et al., *Nature* 327: 70–73 (1987).

*Agrobacterium tumefaciens*-meditated transformation techniques are well described in the scientific literature. See, for example Horsch et al., *Science* 233: 496–498 (1984), and Fraley et al., *Proc. Natl. Acad. Sci.* 80: 4803 (1983).

Although Agrobacterium is useful primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, Vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, *Proc. Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding genes can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp.

3–284 in *The Peptides: Analysis, Synthesis, Biology*, Vol. 2: *Special Methods in Peptide Synthesis, Part A*.; Merrifield, et al., *J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered pyruvate dehydrogenase kinase content or composition). In a preferred embodiment, the seeds would be from corn, soybean, sunflower, sorghum, canola, wheat, alfalfa, cotton, rice, barley and millet.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered phenotype/genotype relative to a control plant (i.e., native, non-transgenic). Back-crossing to a parental plant and out-crossing with a non-transgenic plant are also contemplated.

Modulating Pyruvate Dehydrogenase Kinase Content and/or Composition

The present invention further provides a method for modulating (i.e., increasing or decreasing) pyruvate dehydrogenase kinase content or composition in a plant or part thereof. Modulation can be effected by increasing or decreasing the pyruvate dehydrogenase kinase content (i.e., the total amount of pyruvate dehydrogenase kinase ) and/or the pyruvate dehydrogenase kinase composition (the ratio of various pyruvate dehydrogenase kinase monomers in the plant) in a plant. The method comprises transforming a plant cell with an expression cassette comprising a polynucleotide of the present invention as described above to obtain a transformed plant cell, growing the transformed plant cell under plant forming conditions, and expressing a polynucleotide of the present invention in the plant for a time sufficient to modulate pyruvate dehydrogenase kinase content and/or composition in the plant or plant part.

In some embodiments, carbohydrate metabolism in a plant may be modulated by altering, in vivo or in vitro, the promoter of a non-isolated pyruvate dehydrogenase kinase gene to up- or down-regulate gene expression. In some embodiments, the coding regions of native pyruvate dehydrogenase kinase genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate pyruvate dehydrogenase kinase content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters a re well known in the art. In preferred embodiments, carbon metabolism is modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a pyruvate dehydrogenase kinase gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a pyruvate dehydrogenase kinase gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom an RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs);

5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO97/20078. See also, Zhang, J.-H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polynuculeotide generated from sequence shuffling will have a ligand binding affinity greater than the non-shuffled wild-type polynucleotide. The increase in such properties can be at least 110%, 120%, 130%, 140% or at least 150% of the wild-type value.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a pyruvate dehydrogenase kinase gene or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-pyruvate dehydrogenase kinase genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such a way as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^3$H, $^{125}$I $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^3$H, $^{125}$I $^{35}$S, $^{14}$C, or $^{32}$P, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., *A Colorimetric Method for DNA Hybridization, Nucl. Acids Res.* 12: 3435–3444 (1984)) and synthetic oligonucleotides have been coupled directly with alkaline phosphatase (Jablonski, E., et al., *Preparation of Oligodeoxynucleotide-Alkaline Phosphatase Conjugates and Their Use as Hybrdization Probes, Nuc. Acids. Res.* 14: 6115–6128 (1986); and Li P., et al., *Enzyme-linked Synthetic Oligonucleotide probes: Non-Radioactive Detection of Enterotoxigenic Escherichia Coli in Faeca Specimens, Nucl. Acids Res.* 15: 5275–5287 (1987)).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native pyruvate dehydrogenase kinase protein of 5 amino acids in length or greater and selected from a protein encoded by a polynucleotide of the present invention, such as exemplary sequences of SEQ ID NOS: 2 and 4, are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quaternary structure. Naturally occurring pyruvate dehydrogenase kinase polypeptides can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., *Science* 246: 1275–1281 (1989); and Ward, et al., *Nature* 341: 544–546 (1989); and Vaughan et al., *Nature Biotechnology*, 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14: 845–851 (1996). Also, recombinant immunoglobulins may be produced. See, Cabilly, U.S. Pat. No. 4,816,567; and Queen et al., *Proc. Nat'l Acad. Sci.* 86: 10029–10033 (1989).

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla.

(1987); *Principles and Practice of Immunoassays*, Price and Newman Eds., Stockton Press, NY (1991); and *Non-isotopic Immunoassays*, Ngo, Ed., Plenum Press, NY (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval, et al., *J. Immunol.* 111: 1401–1406 (1973), and Akerstrom, et al., *J. Immuno.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for use in Immunoassays

A protein that specifically binds to or that is specifically immunoreactive with an antibody generated against a defined immunogen, such as an immunogen consisting of the amino acid sequence of SEQ ID NOS: 2 and 4, is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide (e.g., SEQ ID NOS: 2 and 4) is isolated as described herein. For example, recombinant protein can be produced in a mammalian or other eukaryotic cell line. An inbred strain of mice is immunized with the protein of using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570–573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and calorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length pyruvate dehydrogenase kinase polypeptide (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

The following examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

EXAMPLE 1

The polynucleotides having the DNA sequences given in SEQ ID NOS: 1 and 3 were obtained from the sequencing of a library of cDNA clones prepared from maize. The library for PDK1 was constructed from young shoot and for PDK2 from 5 DAP whole kernel. Total RNA was isolated from this tissue using standard protocols and enriched from mRNA by selection with oligo dT, again by standard protocols. This mRNA was then used as template to synthesize complementary DNA (cDNA) using the enzyme reverse transcriptase by conventional methods.

The cDNAs were identified by screening a maize expressed sequence database with the rat pyruvate dehydrogenase kinase polynucleotide sequence, (Popov, K. M. et al., 1993 J. Biol. Chem. 268, 26602–06). Multiple cDNAs with varying degrees of homology were identified using a Basic Local Alignment tool (BLAST). The two unique cDNAs were homologous to the rat PDK sequence with highest overall homology (mostly at the C-terminus). These two unique sequences were not full length, but were used to identify two additional cDNAs of sufficient size to be full length. In this manner the cDNAs with the longest contiguous nucleotide sequence were identified for subsequent sequencing.

MATERIALS AND METHODS

Identification of Maize Pyruvate Dehydrogenase Kinases

The maize cDNAs were identified from a maize expressed sequence tag (EST) database by screening with the entire rat PDK amino acid sequence (10). Multiple cDNAs with varying degrees of homology were identified using the Basic Local Alignment Search Tool (BLAST, 19). Two unique maize cDNAs were homologous to the C-terminal portion of the rat PDK but did not encode for the entire open reading frame. However, these two cDNAs had contiguous sequence with longer cDNAs in this database. In this manner two cDNAs with the longest contiguous nucleotide sequence were identified for subsequent sequencing.

The two cDNAs were sequenced on both strands using AmpliTaq Gold with fluorescent dye-deoxynucleotides according to manufacturers instructions (Applied Biosystems Incorporated, Foster City, Calif.). Automated sequencing was performed at the University of Missouri DNA sequencing core facility. Nested deletions were generated using the "Erase-A-Base" procedure according to manufacturer's instructions (Promega, Madison Wis.).

Preparation of a Mitochondria Matrix Fraction and Kinase-Depleted PDC

Mitochondria were isolated from etiolated maize (B73, Illinois Seed Foundation) shoots according to procedures described previously (20). Isolated mitochondria were resuspended in 30 mM TES-KOH pH 7.5, 2 mM DTT, then homogenized on ice with a Polytron (Brinkmann, Westbury, N.Y.). The homogenate was centrifuged in a TL100 centrifuge at 100 k g in a TL100.3 rotor for 15 min. Supernatants, termed the 100K enzyme, were concentrated with an Amicon ultrafiltration membrane (XM300, 300 kDa cutoff). This protein was layered onto a 10–50% linear glycerol gradient containing 50 mM TES-KOH, pH 7.5 and 2 mM DTT, then centrifuged in an SW28 rotor for 16 h at 25 k rpm. The PDC activity peak at approximately 30% glycerol had only 3% PDK activity and was termed kinase-depleted PDC. PDC activity assays were performed as described previously (20).

Genomic Southern and Northern Blot Analysis

Total DNA was isolated from 10 day old green maize leaves according to standard procedures (21). Digested DNA (20 µg) was separated by electrophoresis in a 0.8% (w/v) agarose gel then transferred to Nytran membranes (Schleicher and Schuell). Following transfer membranes were UV crosslinked and rinsed in 2×SSC, 0.1% (w/v) SDS, prior to prehybridization. Prehybridization was performed at 65 C for 6 h in 2.5×SSPE, 1% (w/v) SDS, 1% nonfat dry milk (Carnation) and 0.025% (w/v) denatured salmon sperm DNA. Hybridization was performed in same solution and at the same temperature, using PDK1 cDNA labeled by random hexamer extension (specific activity=2,500 mCi/mg). Subsequent to hybridization the membrane was washed twice with 2×SSC, 0.1% (w/v) SDS for 1 h then twice with 0.2×SSC, 0.1% (w/v) SDS for 2 h then dried for autoradiography.

Total RNA was isolated from fresh maize tissue according to standard guanidinium extraction procedures (21). RNA (40 µg) samples were separated by electrophoresis in a 1.0% (w/v) agarose gel containing 2.2 M formaldehyde, and subsequently transferred to Nytran membrane. Following transfer the membrane was UV crosslinked and stained with 0.03% w/v methylene blue, 0.3 M sodium acetate, pH 6.0 to visualize RNA markers and rRNA. Hybridization and washing were carried out as described for DNA analysis.

Construction of Expression Plasmids

Primers DDR 193 (5'-gtcacgcccggggaattcaccATGGCGTCGGAGCCGGTGGCG-CGG) and DDR 194 (5'-tcattactcgagctgcag ctatcaTTACGGCAAGGGTTCCTCCGA) were used to amplify PDK1 and PDK2 ORFs corresponding to the region between 56–1098 bp (PDK1) and 78–1172 (PDK2). Restriction sites were introduced into each primer at the 5' end (lowercase letters) to facilitate subcloning of the PCR fragment. The EcoRI (DDR 193) and XhoI (DDR 194) sites were used to subclone the PCR products into pET28a expression vector (Novagen, Madison, Wis.). The EcoRI and PstI (DDR194) sites were used to subclone into pMAL-cRI (New England Biolabs, Beverly, Mass.). To ensure translation termination the two remaining nonsense codons were introduced into DDR194 (underlined). Thermal cycling reactions (50 µl total volume) contained 10 mM Tris-HCl, pH 7.9, 0.5 mM MgCl$_2$, 200 µM dNTPs, 5 units Taq polymerase (Promega, Madison, Wis.), 2 g plasmid cDNA template, 5% dimethyl sulfoxide and 20 pmol of each primer. Cycling conditions were 94 C for 5 min, initial denaturation, followed by 30 cycles of 30 s at 94 C, 30 s at 50 C, 2 min at 72 C with 6 s extensions for the last step of each cycle. Addition of dimethyl sulfoxide was essential for efficient amplification.

Expression and Purification of Recombinant His$_6$-tagged PDK1 Protein and Preparation of Antibodies A single colony of recombinant E coli BL21(DE3) was inoculated into 2 mL of LB medium supplemented with kanamycin (50 µg/mL), and incubated with shaking at 37 C overnight. The cells were transferred to 100 mL of LB plus kanamycin in a baffled Erlenmeyer flask and shaken at 37 C until the $A_{600}$ reached 0.4 (2–4 h). The target gene was induced by adding isopropyl-thiogalactoside to a final concentration of 0.1 mM and continuing shaking at 37 C for another 4–8 h. The cells were harvested and recombinant protein purified by Ni-NTA chelate chromatography under denaturing conditions according to Qiagen (Chatsworth, Calif.) protocols. Dialyzed recombinant protein (50 µg) was emulsified with 0.5 mL of Freund's complete adjuvant (Sigma, St.Louis, Mo.) and injected into New Zealand white rabbits. The rabbits were boosted once with 50 µg of recombinant protein in incomplete adjuvant. SDS-PAGE and immunoblotting were performed as described by Thelen et al. (20).

Immunoprecipitation experiments were carried out with 100K enzyme plus Protein A-purified IgG for 3 h on ice. Protein A-conjugated agarose was then added and incubated for another 3 h. Immunoprecipitates were removed by centrifugation, and the supernatants assayed for MgATP-dependent inactivation of PDC.

Expression and Purification of a MBP-PDK Fusion Protein

The MBP-PDK chimera was expressed similarly to PDK1 in BL21 E. Coli host cells with ampicillin selection. The target gene was induced with 1 mM isopropyl-thiogalactoside for 6 h at 37 C. The cells were harvested and resuspended in ice-cold MBP wash buffer (20 mM Tris HCl, pH 7.4, 0.2 M NaCl, 10 mM 2-mercaptoethanol, 5 mM EDTA) plus 1 mM phenylmethanesulfonyl fluoride, 1 mM benzamidine and 1% (v/v) Triton X-100. The resuspended cells were disrupted by ultrasonic treatment using three 45 s pulses at 50 W, while cooling on ice between pulses. The suspension was centrifuged at 10 k g for 15 min. The supernatant was applied to amylose-resin column (New England Biolabs, Beverly, Mass.) that had been equilibrated with MBP wash buffer. The is column was subsequently washed with 50 volumes of MBP wash buffer. Bound MBP-fusion protein was eluted with 3 volumes of MBP wash buffer plus 1% (w/v) maltose. The purified fusion protein was dialyzed for 16 h in 20 mM TES-KOH pH 7.4, 10% glycerol, 1 mM DTT, 0.1 mM phenylmethanesulfonyl fluoride, and 0.1 mM benzamidine. After dialysis, the fusion protein was concentrated with an Amicon ultrafiltration membrane (PM30, 30 kDa cutoff) and stored at −80 C in 0.1 mL aliquots.

RESULTS AND DISCUSSION

Several conventional approaches were unsuccessful in obtaining cDNA 25 clones encoding plant PDKs. However, two cDNAs encoding putative PDKs were identified from a maize EST database based on sequence similarity to the rat PDK. The two cDNAs[3] are 1332 and 1602 bp in length with open reading frames starting with ATG codons at bases 54 and 78 and in-frame stop codons at 1095 and 1170 bases, respectively. Although no stop codons upstream of the initiating 30 methionine were found, the translation start codon could be predicted when the deduced amino acid sequences of the two maize PDKs were aligned. Furthermore, transcript sizes estimated from northern blot analyses indicated the cDNAs were full length. For clarity we will term the 1332 and 1602 bp cDNAs and the proteins they encode as PDK1 and 2, respectively. These cDNA clones encode polypeptides of 347 and 364 amino acids with calculated molecular weights of 38,867 and 41,327, respectively, and share 77% overall amino acid identity. A major difference between these isoforms is the 16 fewer amino acids (168–183 of PDK2) within PDK1. The function of this domain and reason for its absence in PDK1 are uncertain although it may impart unique properties to this isoform.

The first 30 residues of both PDK1 and 2 are rich in Ala, Arg, and Val residues and can form amphipathic helices. These are characteristic of mitochondrial targeting sequences (22). Another feature is the low abundance of acidic residues, although approximately 40% of plant mitochondrial targeting sequences contain such residues (23) including the maize PDKs which contain three in the first 30 amino acids. Processing generally occurs at sites with Arg residues 3 and 10, 11 amino acids upstream (22, 24). $Arg^8$ and $Arg^{16}$ at the −11 and −3 position may signal processing after $Gly^{18}$. Alternatively, $Arg^{21}$ and $Arg^{28}$ (conserved $Lys^{28}$ for PDK2) are spaced properly and could also signal processing after $Met^{30}$.

The deduced amino acid sequences of the maize PDKs are approximately 30% identical to mammalian PDKs (rat 10, 25; human 15,16). The homologous regions span the entire polypeptide, although the C-terminal half has the highest similarity as illustrated by comparison to the rat PDK. The relatedness of PDKs and procaryotic histidine kinases is confined to five subdomains (11), defined by essential residues also conserved in the maize PDKs. Within subdomain I is a conserved $His^{117}$ (numbering according to PDK2), that in the His kinases is the autophosphorylation site and is involved in phosphotransfer. In mammalian PDKs, e.g. rat, two motifs on either side of this invariant His, $(R^{146}NR^{148})_{rat}$ and $(P^{154}TMAQGV^{160})_{rat}$, are conserved, but not conserved in the BCKDH kinase and are conservatively substituted to $(R^{114}xR^{116})_{maize}$ and $(P^{122}T/AM/IAxGV^{128})_{maize}$ in the maize PDKs. In the mammalian PDKs, the motif $(K^{280}NAMRAT^{286})_{rat}$ containing an essential $Asn^{281}$ within subdomain II of the rat PDK is proposed to be the hinge region allowing the ATP binding domains to interact with the phosphotransfer domain (11). In maize, the canonical Asn is present along with the two basic residues $(K^{242}NxxRAx^{248})$maize. Subdomain III of the rat PDK $(S^{315}DRGGG^{320})_{rat}$, containing the signature DxGxG is also present in both maize PDKs. Subdomain IV contains the essential $Tyr^{279}$ residue within the conserved motif $(F^{293}xYxYSTA^{300})_{maize}$ Subdomain V is defined by a glycine-rich motif $(A^{317}GxGxG^{322})_{maize}$, which like subdomain III has essential Gly residues which may be involved in ATP binding (11).

In addition to the five conserved subdomains characteristic of the procaryotic two-component histidine kinases, the maize PDKs have six other subdomains that are also well-conserved in mammalian PDKs and semi-conserved in the BCKDH kinase. The N-terminal motif $(F^{78}LxxELPV/IRxA^{88})_{rat}$ is conserved in all PDKs and the BCKDH kinase, suggesting that it has a common role in all keto-acid dehydrogenase kinases. The most conserved domain throughout the entire family of polypeptides is not one of the five His-kinase subdomains but rather a 15 amino acid motif between subdomains I and II with the consensus $(F^{151}LDRFYMSRIxIRML^{165})_{maize}$. Interestingly, this motif is located immediately upstream of the 16 "missing" amino acids in PDK1. This motif is less conserved in the BCKDH kinase (FLDxxxxSRxxIRML) suggesting a PDK specific function. Another highly conserved motif is immediately downstream of subdomain V with the consensus $(P^{324}ISRLYAxYFxGDL^{337})_{maize}$, corresponding to (PxSRxYAxYxxGxL) in the BCKDH kinase. Four residues downstream from this motif is the consensus $(S^{341}xEGYGTDA^{349})_{maize}$ for PDKs and (SxxGxGTDx) for the BCKDH kinase. Overall, these four domains in the maize PDKs are more similar to the mammalian PDKs than to the BCKDH kinase further suggesting the maize proteins are PDKs.

An interesting feature of the maize PDK primary sequence is the paucity of Trp and Cys residues. $Trp^{83}$ is conserved in all PDKs but not the BCKDH kinase and is part of the consensus $(V^{80}xxWYxxS^{87})_{maize}$, possibly involved in PDK specific function. $Cys^{206}$, found in the conserved motif $(A^{202}RxxCXXY^{209})_{maize}$ and conserved in all PDKs and the BCKDH kinase, may be involved in catalysis or inter- but probably not intra-thiol disulfide exchange since PDK1 does not contain a second Cys.

Phylogenetic tree analysis with putative and characterized PDKs reveals at least three groups of related PDKs. The putative A. suum and hypothetical C. elegans proteins form a group that may also contain the putative D. melanogaster PDK. The characterized mammalian PDKs form a closely linked group more related to the other animal than the plant PDKs. The BCKDH kinase is divergent from all PDKs and the procaryotic His-kinase PhoM (26) outlies the entire group.

Southern blot analysis, under high stringency conditions, shows two prevalent bands with all restriction enzymes indicating the presence of two related genes. Northern blot analysis shows an abundant 1.6 kb transcript in leaves and roots. A second 1.3 kb transcript is present in low abundance in leaves and absent in roots. By comparison with the two cDNAs the 1.3 and 1.6 kb transcripts likely correspond to PDK1 and 2, respectively. Since PDK1 transcript was observed in green leaves but not roots it might be a tissue specific or inducible isoform. Interestingly, both PDK transcripts were more abundant in leaves than roots which may indicate a tissue-specific role for these kinases. Perhaps the high expression of PDKs in green leaves enables acute response to mitochondrial ATP concentration during photosynthesis; a model consistent with the photosynthetic-induced inhibition of mtPDC activity observed in maize and other plants (7, 8).

Recombinant $His_6$-tagged PDK1 expressed in E. coli was greater than 95% insoluble under all conditions tested, therefore it was purified under denaturing conditions. Purified recombinant $His_6$-tagged PDK1 and 2 migrated at 43 and 45 kDa, respectively. The recombinant proteins were slightly larger than the predicted mass of 38,867 and 41,327 Da because the $His_6$ and epitope tags at the 25 N-terminus of the recombinant proteins add approximately 3.5 kDa. Recombinant PDK1 was used as antigen to raise rabbit polyclonal antibodies. Antibodies to PDK1 recognized both PDK recombinant proteins by immunoblot analysis (data not shown). Purified IgG immunoprecipitated 75% of PDK activity from a 100K maize mitochondrial extract while the preimmune IgG had no effect. The non-precipitated kinase activity might be due to an immunogenically distinct kinase or incomplete precipitation. PDK1 antibodies did not recognize any polypeptides from a total maize mitochondrial fraction. However, upon enrichment for PDC activity by rate-zonal sedimentation a 41 kDa polypeptide was decorated with PDK antibodies. This polypeptide was not detected with the PDC activity after glycerol gradient fractionation, in agreement with the loss of kinase activity in this fraction. The smaller size of the 41 kDa mitochondrial matrix protein, compared to recombinant PDKs, is likely due to the absence of a $His_6$ and epitope tags and processing of the mitochondrial targeting peptide. In previous reports the $M_r$ of PDK from pea leaves was estimated as 53.3 kDa (27, 28) considerably larger than the maize PDKs. The size of pea leaf PDK suggests that these proteins may be less conserved among plants.

The solubility problem associated with the pET expression system was overcome by expressing PDK as a C-terminal fusion to MBP. Purified recombinant MBP-PDK2 inactivated kinase-depleted maize mitochondrial PDC in an ATP-dependent manner while purified MBP had no effect (data not shown). During the same time period kinase-depleted PDC had 3% kinase activity. For ATP-dependent inactivation, the ratio of PDK to PDC was approximately 1:30 (µg) taking into consideration the purity of the PDC preparation (20) and the non-catalytic 46 kDa MBP partner protein. The rate of ATP-dependent inactivation was slower with recombinant MBP-PDK2 than with native PDK (20) presumably due to the bulk of the MBP protein partner. The MBP-PDK2 mediated MgATP-dependent inactivation was coincident with $^{32}P$ incorporation from $[-^{32}P]$ ATP into a 43 kDa protein, the precise molecular mass for maize E1 as determined using monoclonal antibodies to maize E1 (20).

The data presented here support our conclusion that maize PDK1 and 2 are PDK and not BCKDH kinase isoforms. In summary, the evidence for this is 1) the primary amino acid sequences are more similar to mammalian PDKs than to the BCKDH kinase, 2) anti-PDK antibodies immunoprecipitate PDK activity from a maize mitochondrial extract, and 3) recombinant PDK inactivates kinase-depleted maize mitochondrial PDC with concomitant incorporation of phosphate on to the 43 kDa E1 subunit.

REFERENCES

1. Reed, L. J. (1974) *Acc. Chem. Res.* 7, 40–56
2. Patel, M. S., and Roche, T. E. (1990) *FASEB J.* 4, 3224–3233
3. Camp, P. J., and Randall, D. D. (1985) *Plant Physiol.* 77, 571–577
4. Williams, M., and Randall, D. D. (1979) *Plant Physiol.* 64, 1099–1103
5. Luethy, M. H., Miernyk, J. A., David, N. R., and Randall, D. D. (1996) Alpha-Keto Acid Dehydrogenase Complexes pp 71–72, Birkhausen, Boston
6. Randall, D. D., Miernyk, J. A., David, N. R., Gemel, J., and Luethy, M. H. (1996) *Protein Phosphorylation in Plants*, pp. 87–103, Clarendon Press, Oxford
7. Budde, R. J. A., and Randall, D. D. (1990) *Proc. Natl. Acad. Sci. U.S.A.* 87, 673–676
8. Gemel, J., and Randall, D. D. (1992) *Plant Physiol.* 100, 908–914
9. Schuller, K. A., Gemel, J., and Randall, D. D. (1993) *Plant Physiol.* 102, 139–143
10. Popov, K. M., Kedishvili, N. Y., Zhao, Y., Shimomura, Y., Crabb, D. W., and Harris R. A. (1993) *J.Biol. Chem.* 268, 26602–26606
11. Harris, R. A., Popov, K. M., Zhao, Y., Kedishvili, N. Y., Shimomura, Y., and Crabb, D. W. (1995) *Advan. Enzyme Regul.* 35, 147–162
12. Stock, J. B., Ninfa, A. J., and Stock, A. M. (1989) *Microbiol. Rev.* 53, 450–490
13. Popov, K. M., Zhao, Y., Shimomura, Y., Kuntz, M. J., and Harris, R. A. (1992) *J. Biol. Chem.* 267, 13127–13130
14. Popov, K. M., Shimomura, Y., and Harris, R. A. (1991) *Protein Expression Purif.* 2, 278–286
15. Gudi, R., Bowker-Kinley, M. M., Kedishvili, N. Y., Zhao, Y., and Popov, K. M. (1995) *J. Biol. Chem.* 270, 28989–28994
16. Rowles, J., Scherer, S. W., Xi, T., Majer, M., Nickle, D. C., Rommens, J. M., Popov, K. M., Harris, R. A., Riebow, N. L., Xia, J., Tsui, L., Bogardus, C., and Prochazka, M. (1996) *J. Biol. Chem.* 271, 22376–22382
17. Katsube, T., Nomoto, S., Togashi, S., Ueda, R., Kobayashi, M., and Takahisa, M. (1997) *DNA Cell Biol.* 16, 335–339
18. Wilson, R., Ainscough, R., Anderson, K., Baynes, C., Berks, M., Bonfield, J., Burton, J., Connell, M., Copsey, T., Cooper, J., Coulson, A., Craxton, M.Dear, S., Du, Z., Durbin, R., Favello, A., Fraser, A., Fulton, L., Gardner, A., Green, P., Hawkins, T., Hillier, L., Jier, M., Johnston, L., Jones, M., Kershaw, J., Kirsten, J., Laisster, N., Latreille, P., Lightning, J., Lloyd, C., Mortimore, B., O'Callaghan, M., Parsons, J., Percy, C., Rifken, L., Roopra, A., Saunders, D., Shownkeen, R., Sims, M., Smaldon, N., Smith, A., Smith, M., Sonnhammer, E., Staden, R., Sulston, J., Thierry-Mieg, J., Thomas, K., Vaudin, M., Vaughan, K., Waterson, R., Watson, A., Weinstock, L., Wilkinson-Sproat, J., and Wohidman, P. (1994) *Nature* 368, 32–38
19. Altschul, S. F., Gish, W., Miller, W., Myers, E. W., and Lipman, D. J. (1990) *J. Mol. Biol.* 215, 403–410
20. Thelen, J. J. Miernyk, J. A., and Randall, D. D. (1997) *Plant Physiol.* In press
21. Sambrook, J., Fritsch, E. F., and Maniatis, T. (1989) *Molecular Cloning:A Laboratory Manual*, Cold Spring Harbor Laboratory, Cold Spring Harbor, N.Y.
22. Moore, A. L., Wood, C. K., and Watts, F. Z. (1994) *Annu. Rev. Plant Physiol. Plant Mol. Biol.* 45, 545–575
23. Whelan, J., and Glaser, E. (1997) *Plant Mol. Biol.* 33, 771–789
24. von Heijne, G., Steppuhn, J., and Herrmann, R. G. (1989) *Eur. J. Biochem.* 180, 535–545
25. Popov, K. M., Kedishvili, N. Y., Zhao, Y., Gudi, R., and Harris, R. A. (1994) *J. Biol. Chem.* 269, 29720–29724
26. Amemura, M., Makino, K., Shinagawa, H., and Nakata, A. (1990) *J. Bacteriol.* 172, 6300–6307
27. Miernyk, J. A., Rapp, B. J., David, N. R., and Randall, D. D. (1987) *In: Plant Mitochondria*, eds A. L. Moore and R. B. Beechey, pp.189–197, Plenum Publishing
28. Miernyk, J. A., and Randall, D. D. (1987) *In: Plant Mitochondria*, eds A. L. Moore and R. B. Beechey, pp. 223–226, Plenum Publishing

What is claimed is:

1. An isolated pyruvate dehydrogenase kinase polynucleotide comprising a member selected from the group consisting of:
   (a) a polynucleotide that encodes the polypeptide of SEQ ID NO: 2 or 4;
   (b) a polynucleotide comprising the sequence set forth in the encoding region of SEQ ID NO:1 OR 3; and
   (c) a polynucleotide complimentary to a polynucleotide of any one of (a) or (b).

2. An isolated nucleic acid according to claim 1 comprising the sequence set forth in SEQ ID NO: 1 or 3.

3. A vector comprising at least one nucleic acid of claim 1.

4. An expression cassette comprising at least one nucleic acid of claim 1 operably linked to a promoter, wherein the nucleic acid is in sense or antisense orientation.

5. A host cell into which is introduced at least one expression cassette of claim 4.

6. The host cell of claim 5 that is a plant cell.

7. A transgenic plant comprising at least one expression cassette of claim 4.

8. The transgenic plant of claim 7, wherein the plant is selected from the group consisting of: corn, soybean, sunflower, sorghum, canola, wheat, alfalfa, cotton, rice, barley and millet.

9. A seed from the transgenic plant of claim 7.

10. The seed of claim 9, wherein the seed is selected from the group consisting of: corn, soybean, sunflower, sorghum, canola, wheat, alfalfa, cotton, rice, barley and millet.

11. An isolated ribonucleic acid sequence encoding a polypeptide comprising a member selected from the group consisting of:
   (a) a polypeptide comprising at least 15 contiguous amino acids of SEQ ID NO: 2 or 4; and
   (b) a polypeptide comprising at least 60% sequence identity to SEQ ID NO: 2 or 4;
wherein the percent of sequence identity is based on the entire sequence and is determined by blast 2.0 using default parameters; wherein the polypeptide of (a) or (b) is a monocot PDK polypeptide.

12. A method of modulating the level of PDK protein in a plant, comprising:
   a) stably transforming a plant cell with a monocot PDK polynucleotide operably linked to a promoter, wherein the polynucleotide is in sense or antisense orientation;
   b) growing the plant cell under plant growing conditions to produce a regenerated plant; capable of expressing the polynucleotide for a time sufficient to modulate the PDK protein in the plant.

13. The method of claim 12, wherein the PDK polynucleotide is selected from those of claim 1.

14. The method of claim 12, wherein the plant is selected from the group consisting of: corn, soybean, sunflower, sorghum, canola, wheat, alfalfa, cotton, rice, barley and millet.

15. The method of claim 12, wherein PDK protein is increased.

16. The method of claim 12, wherein PDK protein is decreased.

17. A method for controlling carbon flow into the Krebs cycle in plants comprising modulating PDK protein expression by the method of claim 12.

18. A method for increasing oil content in a plant by modulating PDK protein expression by the method of claim 14.

19. An isolated pyruvate dehydrogenase kinase polynucleotide comprising a member selected from the group consisting of:
   (a) a polynucleotide comprising at least 30 contiguous bases of the encoding region of SEQ ID NOS: 1 or 3; and
   (b) a polynucleotide complimentary to a polynucleotide of (a); wherein (a) encodes a monocot pyruvate dehydrogenase kinase.

20. An isolated pyruvate dehydrogenase kinase polynucleotide comprising a member selected from the group consisting of:
   (a) a polynucleotide having at least 60% sequence identity to SEQ ID NOS: 1 or 3, wherein the % sequence identity is based on the entire encoding region and is determined by BLAST 2.0 under default parameters; and
   (b) a polynucleotide complimentary to a polynucleotide of (a); wherein (a) encodes a monocot pyruvate dehydrogenase kinase.

21. A vector comprising at least one nucleic acid of claim 20.

22. An expression cassette comprising at least one nucleic acid of claim 20 operably linked to a promoter, wherein the nucleic acid is in sense or antisense orientation.

23. A host cell into which is introduced at least one expression cassette of claim 22.

24. The host cell of claim 23 that is a plant cell.

25. A transgenic plant comprising at least one expression cassette of claim 22.

26. The transgenic plant of claim 25, wherein the plant is selected from the group consisting of: corn, soybean, sunflower, sorghum, canola, wheat, alfalfa, cotton, rice, barley and millet.

27. A seed from the transgenic plant of claim 25.

28. The seed of claim 27, wherein the seed is selected from the group consisting of: corn, soybean, sunflower, sorghum, canola, wheat, alfalfa, cotton, rice, barley and millet.

29. An isolated pyruvate dehydrogenase kinase polynucleotide comprising a member selected from the group consisting of:
  (a) a polynucleotide comprising at least 30 nucleotides in length which hybridizes under moderate stringency conditions to a polynucleotide having the sequence set forth in the encoding region of SEQ ID NO: 1 or 3, wherein the conditions include hybridization in 40 to 45% formamide, 1 M NaCl, 1% SDS at 37° C. and a wash in 0.5× to 1×SSC at 55 to 60° C.; and
  (b) a polynucleotide complimentary to a polynucleotide of (a); wherein (a) encodes a monocot pyruvate dehydrogenase kinase.

30. A vector comprising at least one nucleic acid of claim 29.

31. An expression cassette comprising at least one nucleic acid of claim 29 operably linked to a promoter, wherein the nucleic acid is in sense or antisense orientation.

32. A host cell into which is introduced at least one expression cassette of claim 31.

33. The host cell of claim 32 that is a plant cell.

34. A transgenic plant comprising at least one expression cassette of claim 31.

35. The transgenic plant of claim 34, wherein the plant is selected from the group consisting of: corn, soybean, sunflower, sorghum, canola, wheat, alfalfa, cotton, rice, barley and millet.

36. A seed from the transgenic plant of claim 35.

37. The seed of claim 36, wherein the seed is selected from the group consisting of: corn, soybean, sunflower, sorghum, canola, wheat, alfalfa, cotton, rice, barley and millet.

38. An isolated pyruvate dehydrogenase kinase polynucleotide comprising a member selected from the group consisting of:
  (a) a polynucleotide amplified from a *Zea mays* nucleic acid library using the primers of SEQ ID NOS: 5 and 6; and
  (b) a polynucleotide complimentary to a polynucleotide of (a); wherein (a) encodes a monocot pyruvate dehydrogenase kinase.

39. A vector comprising at least one nucleic acid of claim 38.

40. An expression cassette comprising at least one nucleic acid of claim 38 operably linked to a promoter, wherein the nucleic acid is in sense or antisense orientation.

41. A host cell into which is introduced at least one expression cassette of claim 40.

42. The host cell of claim 41 that is a plant cell.

43. A transgenic plant comprising at least one expression cassette of claim 40.

44. The transgenic plant of claim 43, wherein the plant is selected from the group consisting of: corn, soybean, sunflower, sorghum, canola, wheat, alfalfa, cotton, rice, barley and millet.

45. A seed from the transgenic plant of claim 43.

46. The seed of claim 45, wherein the seed is selected from the group consisting of: corn, soybean, sunflower, sorghum, canola, wheat, alfalfa, cotton, rice, barley and millet.

47. The isolated pyruvate dehydrogenase kinase polynucleotide of claim 20 wherein the polynucleotide comprises a member selected from the group consisting of:
  (a) a polynucleotide having at least 70% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

48. The isolated pyruvate dehydrogenase kinase polynucleotide of claim 20 wherein the polynucleotide comprises a member selected from the group consisting of:
  (a) a polynucleotide having at least 75% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

49. The isolated pyruvate dehydrogenase kinase polynucleotide of claim 20 wherein the polynucleotide comprises a member selected from the group consisting of:
  (a) a polynucleotide having at least 80% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

50. The isolated pyruvate dehydrogenase kinase polynucleotide of claim 20 wherein the polynucleotide comprises a member selected from the group consisting of:
  (a) a polynucleotide having at least 85% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

51. The isolated pyruvate dehydrogenase kinase polynucleotide of claim 20 wherein the polynucleotide comprises a member selected from the group consisting of:
  (a) a polynucleotide having at least 90% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

52. The isolated pyruvate dehydrogenase kinase polynucleotide of claim 20 wherein the polynucleotide comprises a member selected from the group consisting of:
  (a) a polynucleotide having at least 95% sequence identity to SEQ ID NOS: 1 or 3, wherein the % sequence identity is based on the entire encoding region and is determined by BLAST 2.0 under default parameters, and
  (b) a polynucleotide complimentary to a polynucleotide of (a); wherein (a) encodes a monocot pyruvate dehydrogenase kinase.

* * * * *

SEQUENCE LISTING

<160> NUMBER OF SEQ ID NOS: 6

<210> SEQ ID NO 1
<211> LENGTH: 1332
<212> TYPE: DNA
<213> ORGANISM: Zea mays
<220> FEATURE:
<221> NAME/KEY: CDS
<222> LOCATION: (55)...(1095)

<400> SEQUENCE: 1

```
ccacgcgtcc gccaatttcc acaaacctcg cgcgcggcgg agggagaagg aagg atg         57
                                                            Met
                                                             1 gcg tcg gag ccg gtg gcg cgg gcg gtg gcg gag gag gtg gcg cgc tgg        105
Ala Ser Glu Pro Val Ala Arg Ala Val Ala Glu Glu Val Ala Arg Trp
         5                  10                  15 ggc gcg atg cgc cag acc ggg gtc agc ctg cgc tac atg atg gag ttc        153
Gly Ala Met Arg Gln Thr Gly Val Ser Leu Arg Tyr Met Met Glu Phe
     20                  25                  30 ggg gcg cgc ccc acg gag cgg acc ctc ctt ctc gcc gcg cag ttc ctg        201
Gly Ala Arg Pro Thr Glu Arg Thr Leu Leu Leu Ala Ala Gln Phe Leu
 35                  40                  45 cac aag gag ctc ccc atc cgc atc gcg cga cgg gcg ctc gac ctc gac        249
His Lys Glu Leu Pro Ile Arg Ile Ala Arg Arg Ala Leu Asp Leu Asp
 50                  55                  60                  65 tcg ctc ccc ttc ggc ctc tcc acc aag ccc gcc atc ctc aag gtg aaa        297
Ser Leu Pro Phe Gly Leu Ser Thr Lys Pro Ala Ile Leu Lys Val Lys
             70                  75                  80 gat tgg tat gtg gag tca ttc cgt gaa atc cgg tcc ttt cca gag gtg        345
Asp Trp Tyr Val Glu Ser Phe Arg Glu Ile Arg Ser Phe Pro Glu Val
         85                  90                  95 agg aac cag aaa gat gag ctc gcc ttc acc cag atg atc aaa atg atc        393
Arg Asn Gln Lys Asp Glu Leu Ala Phe Thr Gln Met Ile Lys Met Ile
    100                 105                 110 agg gta cga cac acc aat gtg gtg cct gcg att gca ttg ggt gtg cag        441
Arg Val Arg His Thr Asn Val Val Pro Ala Ile Ala Leu Gly Val Gln
115                 120                 125 cag ctg aag aag gac ttg ggc ggt cca aag gcg ttc ccc ccc gga atc        489
Gln Leu Lys Lys Asp Leu Gly Gly Pro Lys Ala Phe Pro Pro Gly Ile
130                 135                 140                 145 cat gag atc cat cag ttt ctt gac cgc ttc tac atg tca agg att ggg        537
His Glu Ile His Gln Phe Leu Asp Arg Phe Tyr Met Ser Arg Ile Gly
                150                 155                 160 atc cgg atg ctg ata ggg ctt ata aac aca aaa atg tca ccc atg aca        585
Ile Arg Met Leu Ile Gly Leu Ile Asn Thr Lys Met Ser Pro Met Thr
            165                 170                 175 gtt gct cga att gct agt gaa gat gca cgt gct att tgc atg cgg gag        633
Val Ala Arg Ile Ala Ser Glu Asp Ala Arg Ala Ile Cys Met Arg Glu
        180                 185                 190 tat gga tca tct cct gat gtc gac ata tat ggt gat ccg ggt ttt aca        681
Tyr Gly Ser Ser Pro Asp Val Asp Ile Tyr Gly Asp Pro Gly Phe Thr
    195                 200                 205 ttt cca tat gtt aca cca cat cta cat ctc atg att ttc gag ctg gtg        729
Phe Pro Tyr Val Thr Pro His Leu His Leu Met Ile Phe Glu Leu Val
210                 215                 220                 225 aag aac tcc ctt cgc gcg gta cag gaa cgg tat atg gat tct gat aag        777
Lys Asn Ser Leu Arg Ala Val Gln Glu Arg Tyr Met Asp Ser Asp Lys
                230                 235                 240
```

```
ctt gca cct cca gtt cga atc ata gtt gct gat gga gca gag gat gta    825
Leu Ala Pro Pro Val Arg Ile Ile Val Ala Asp Gly Ala Glu Asp Val
            245                 250                 255 act att aag att agt gat gaa ggt ggt gga ata cca agg agt ggg ctc    873
Thr Ile Lys Ile Ser Asp Glu Gly Gly Gly Ile Pro Arg Ser Gly Leu
            260                 265                 270 tca aga att ttt acg tat ctc tat agt aca gca gaa aac cct cct gat    921
Ser Arg Ile Phe Thr Tyr Leu Tyr Ser Thr Ala Glu Asn Pro Pro Asp
        275                 280                 285 ctg gac gga cat aat gaa gga gta act atg gct gga tat ggt tat ggg    969
Leu Asp Gly His Asn Glu Gly Val Thr Met Ala Gly Tyr Gly Tyr Gly
290                 295                 300                 305 atc cct att agt cgc ctt tat gct cga tat ttc ggt ggg gac ttg cag   1017
Ile Pro Ile Ser Arg Leu Tyr Ala Arg Tyr Phe Gly Gly Asp Leu Gln
                310                 315                 320 atc atc tct atg gaa gga tat gga act gat gct tac ctc cac ctt tca   1065
Ile Ile Ser Met Glu Gly Tyr Gly Thr Asp Ala Tyr Leu His Leu Ser
                325                 330                 335 cgg ctg gga gat tcg gag gaa ccc ttg ccg taatttattc aaaagaacca     1115
Arg Leu Gly Asp Ser Glu Glu Pro Leu Pro
                340                 345 ttcctgtaat taggatattg cttctgtgct ggtatgcaag tatagttctg aaggccagcc  1175
acctgttcag ctgttcgtgt ccctacttgt tgtctttatt gttcattcat catcttaatg  1235
gattgtgatc gtaattccta atcgttttat gactgatttg tactgtcaaa aaaaaaaaa   1295 aaaaaaaaaa aaaaaaaaaa aaaaaaaaaa aaaaaaa                           1332

<210> SEQ ID NO 2
<211> LENGTH: 347
<212> TYPE: PRT
<213> ORGANISM: Zea mays

<400> SEQUENCE: 2

Met Ala Ser Glu Pro Val Ala Arg Ala Val Ala Glu Glu Val Ala Arg
 1               5                  10                  15

Trp Gly Ala Met Arg Gln Thr Gly Val Ser Leu Arg Tyr Met Met Glu
            20                  25                  30

Phe Gly Ala Arg Pro Thr Glu Arg Thr Leu Leu Leu Ala Ala Gln Phe
        35                  40                  45

Leu His Lys Glu Leu Pro Ile Arg Ile Ala Arg Arg Ala Leu Asp Leu
    50                  55                  60

Asp Ser Leu Pro Phe Gly Leu Ser Thr Lys Pro Ala Ile Leu Lys Val
65                  70                  75                  80

Lys Asp Trp Tyr Val Glu Ser Phe Arg Glu Ile Arg Ser Phe Pro Glu
                85                  90                  95

Val Arg Asn Gln Lys Asp Glu Leu Ala Phe Thr Gln Met Ile Lys Met
            100                 105                 110

Ile Arg Val Arg His Thr Asn Val Val Pro Ala Ile Ala Leu Gly Val
        115                 120                 125

Gln Gln Leu Lys Lys Asp Leu Gly Gly Pro Lys Ala Phe Pro Pro Gly
    130                 135                 140

Ile His Glu Ile His Gln Phe Leu Asp Arg Phe Tyr Met Ser Arg Ile
145                 150                 155                 160

Gly Ile Arg Met Leu Ile Gly Leu Ile Asn Thr Lys Met Ser Pro Met
                165                 170                 175

Thr Val Ala Arg Ile Ala Ser Glu Asp Ala Arg Ala Ile Cys Met Arg
            180                 185                 190
```

```
Glu Tyr Gly Ser Ser Pro Asp Val Asp Ile Tyr Gly Asp Pro Gly Phe
            195                 200                 205

Thr Phe Pro Tyr Val Thr Pro His Leu His Leu Met Ile Phe Glu Leu
    210                 215                 220

Val Lys Asn Ser Leu Arg Ala Val Gln Glu Arg Tyr Met Asp Ser Asp
225                 230                 235                 240

Lys Leu Ala Pro Pro Val Arg Ile Ile Val Ala Asp Gly Ala Glu Asp
                245                 250                 255

Val Thr Ile Lys Ile Ser Asp Glu Gly Gly Ile Pro Arg Ser Gly
                260                 265                 270

Leu Ser Arg Ile Phe Thr Tyr Leu Tyr Ser Thr Ala Glu Asn Pro Pro
        275                 280                 285

Asp Leu Asp Gly His Asn Glu Gly Val Thr Met Ala Gly Tyr Gly Tyr
    290                 295                 300

Gly Ile Pro Ile Ser Arg Leu Tyr Ala Arg Tyr Phe Gly Gly Asp Leu
305                 310                 315                 320

Gln Ile Ile Ser Met Glu Gly Tyr Gly Thr Asp Ala Tyr Leu His Leu
                325                 330                 335

Ser Arg Leu Gly Asp Ser Glu Glu Pro Leu Pro
        340                 345
```

<210> SEQ ID NO 3
<211> LENGTH: 1602
<212> TYPE: DNA
<213> ORGANISM: Zea mays
<220> FEATURE:
<221> NAME/KEY: CDS
<222> LOCATION: (78)...(1169)

<400> SEQUENCE: 3

```
ggcacgaggt ggcttggcag tgtcgatcgc tgatcccacc ggctgataga gttggcggcc      60
gggagagtga gtcaggg atg gcg tcg gag ccg gtg gcg cgg gcg gtg gcg         110
                Met Ala Ser Glu Pro Val Ala Arg Ala Val Ala
                 1               5                  10 gag gag gtg ggc cgc tgg ggc agc atg aag cag acg ggg gtg acc ctg        158
Glu Glu Val Gly Arg Trp Gly Ser Met Lys Gln Thr Gly Val Thr Leu
             15                  20                  25 cgg tac atg atg gag ttc ggc tcc cgc ccc acc cag cgc aac ctg ctc        206
Arg Tyr Met Met Glu Phe Gly Ser Arg Pro Thr Gln Arg Asn Leu Leu
         30                  35                  40 ctc tcc gcg cag ttc ctg cac aag gag ctc ccc atc cgc ttc gcg cgc        254
Leu Ser Ala Gln Phe Leu His Lys Glu Leu Pro Ile Arg Phe Ala Arg
     45                  50                  55 cgc gcg ctc gag ctc gac tcg ctg ccc ttc ggc ctc tcc aac aag ccc        302
Arg Ala Leu Glu Leu Asp Ser Leu Pro Phe Gly Leu Ser Asn Lys Pro
 60                  65                  70                  75 gcc atc ctc aag gtg cgg gac tgg tac ttg gac tca ttc cgg gac atc        350
Ala Ile Leu Lys Val Arg Asp Trp Tyr Leu Asp Ser Phe Arg Asp Ile
                 80                  85                  90 aga tac ttc cct gaa gtg agg agc cgg aac gac gag ctc gct ttc acg        398
Arg Tyr Phe Pro Glu Val Arg Ser Arg Asn Asp Glu Leu Ala Phe Thr
             95                 100                 105 cag atg atc aat atg gtc aag gtg cgg cat aac aat gtg gtt cca acc        446
Gln Met Ile Asn Met Val Lys Val Arg His Asn Asn Val Val Pro Thr
        110                 115                 120 atg gcc ttg gga gtg cag cag ctg aag aag gag ctg ggc cgc tca agg       494
Met Ala Leu Gly Val Gln Gln Leu Lys Lys Glu Leu Gly Arg Ser Arg
    125                 130                 135
```

```
aag gtt cca ttc gag ttc gat gag atc gac gag ttc ctt gac cgg ttc    542
Lys Val Pro Phe Glu Phe Asp Glu Ile Asp Glu Phe Leu Asp Arg Phe
140                 145                 150                 155 tac atg tca agg att ggc atc cgc atg ctg ata ggg cag cat gtg gct    590
Tyr Met Ser Arg Ile Gly Ile Arg Met Leu Ile Gly Gln His Val Ala
            160                 165                 170 ttg cat gac cct aaa ccg gag cct ggt gtt ata ggc ctc atc aat aca    638
Leu His Asp Pro Lys Pro Glu Pro Gly Val Ile Gly Leu Ile Asn Thr
                175                 180                 185 aga tta tcc cca atc cag gtg gct caa gct gct tgt gaa gat gcc cgt    686
Arg Leu Ser Pro Ile Gln Val Ala Gln Ala Ala Cys Glu Asp Ala Arg
            190                 195                 200 tct gtc tgt tta agg gaa tat gga tca gct cct gat att aac att tat    734
Ser Val Cys Leu Arg Glu Tyr Gly Ser Ala Pro Asp Ile Asn Ile Tyr
205                 210                 215 ggc gat cca aat ttt acg ttt cca tac gtc aca tta cac cta cac ctg    782
Gly Asp Pro Asn Phe Thr Phe Pro Tyr Val Thr Leu His Leu His Leu
220                 225                 230                 235 atg tta ttt gaa ttg gtg aag aac tct ctc cgc gcg gtg caa gaa cgg    830
Met Leu Phe Glu Leu Val Lys Asn Ser Leu Arg Ala Val Gln Glu Arg
                240                 245                 250 tat atg aac tct gat aaa gat gtt ccc ccg gtt aga att ata gtt gct    878
Tyr Met Asn Ser Asp Lys Asp Val Pro Pro Val Arg Ile Ile Val Ala
            255                 260                 265 gat gga gaa gag gat gtt act atc aag gtt agc gat gaa ggt ggc ggg    926
Asp Gly Glu Glu Asp Val Thr Ile Lys Val Ser Asp Glu Gly Gly Gly
        270                 275                 280 ata cca aga agc ggc ctc ccg aga att ttc acg tat ctg tac agc acc    974
Ile Pro Arg Ser Gly Leu Pro Arg Ile Phe Thr Tyr Leu Tyr Ser Thr
285                 290                 295 gca aag aat cct cct gag cta gat aga cct aat act gaa agg gta act    1022
Ala Lys Asn Pro Pro Glu Leu Asp Arg Pro Asn Thr Glu Arg Val Thr
300                 305                 310                 315 atg gct ggg tat ggt ttc ggg ctc ccg atc agc cga ctc tac gct cgg    1070
Met Ala Gly Tyr Gly Phe Gly Leu Pro Ile Ser Arg Leu Tyr Ala Arg
            320                 325                 330 tat ttt ggc ggc gac ctg caa atc atc tcg atg gaa gga tac ggt acc    1118
Tyr Phe Gly Gly Asp Leu Gln Ile Ile Ser Met Glu Gly Tyr Gly Thr
                335                 340                 345 gat gct tac ctc cac ttg tcg cgg ctg gga gat tca gag gag ccc ttg    1166
Asp Ala Tyr Leu His Leu Ser Arg Leu Gly Asp Ser Glu Glu Pro Leu
            350                 355                 360 cct tgacgacata tttttgtgga cctccagtac cactcttctc ctgtaactat         1219
Pro gtggctcgat cttcttgtaa tccagtgctg gcctcgacct atatatatat agctatagtt  1279
ggcctcgacc ttatttcact gcctgctctg ctgcattgtg aacacagcac tgctacgtcc  1339
tgcttacttc cgccatgtac tatgatctct ctgccggcct tcaacaggaa aaagaaagg   1399 acgagggaaa tcatggggag cagctaggcg gatgagcgca ttctcggtag ctgctaatct  1459
cattttcata gctgcgtctc ttgtgttgta cattacatag tctggatttg agcttttgct  1519
atggcaagta tcacatgtta cctgggtaat tgagaaatat aagtaaaaaa aacagtaaaa  1579
aaaaaaaaaa aaaaaaaaa aaa                                          1602

<210> SEQ ID NO 4
<211> LENGTH: 364
<212> TYPE: PRT
<213> ORGANISM: Zea mays
```

```
<400> SEQUENCE: 4

Met Ala Ser Glu Pro Val Ala Arg Ala Ala Glu Glu Val Gly Arg
 1               5                  10                  15

Trp Gly Ser Met Lys Gln Thr Gly Val Thr Leu Arg Tyr Met Met Glu
                20                  25                  30

Phe Gly Ser Arg Pro Thr Gln Arg Asn Leu Leu Leu Ser Ala Gln Phe
            35                  40                  45

Leu His Lys Glu Leu Pro Ile Arg Phe Ala Arg Arg Ala Leu Glu Leu
        50                  55                  60

Asp Ser Leu Pro Phe Gly Leu Ser Asn Lys Pro Ala Ile Leu Lys Val
65                  70                  75                  80

Arg Asp Trp Tyr Leu Asp Ser Phe Arg Asp Ile Arg Tyr Phe Pro Glu
                85                  90                  95

Val Arg Ser Arg Asn Asp Glu Leu Ala Phe Thr Gln Met Ile Asn Met
            100                 105                 110

Val Lys Val Arg His Asn Asn Val Val Pro Thr Met Ala Leu Gly Val
            115                 120                 125

Gln Gln Leu Lys Lys Glu Leu Gly Arg Ser Arg Lys Val Pro Phe Glu
    130                 135                 140

Phe Asp Glu Ile Asp Glu Phe Leu Asp Arg Phe Tyr Met Ser Arg Ile
145                 150                 155                 160

Gly Ile Arg Met Leu Ile Gly Gln His Val Ala Leu His Asp Pro Lys
                165                 170                 175

Pro Glu Pro Gly Val Ile Gly Leu Ile Asn Thr Arg Leu Ser Pro Ile
            180                 185                 190

Gln Val Ala Gln Ala Ala Cys Glu Asp Ala Arg Ser Val Cys Leu Arg
    195                 200                 205

Glu Tyr Gly Ser Ala Pro Asp Ile Asn Ile Tyr Gly Asp Pro Asn Phe
210                 215                 220

Thr Phe Pro Tyr Val Thr Leu His Leu His Leu Met Leu Phe Glu Leu
225                 230                 235                 240

Val Lys Asn Ser Leu Arg Ala Val Gln Glu Arg Tyr Met Asn Ser Asp
                245                 250                 255

Lys Asp Val Pro Pro Val Arg Ile Ile Val Ala Asp Gly Glu Glu Asp
            260                 265                 270

Val Thr Ile Lys Val Ser Asp Glu Gly Gly Ile Pro Arg Ser Gly
        275                 280                 285

Leu Pro Arg Ile Phe Thr Tyr Leu Tyr Ser Thr Ala Lys Asn Pro Pro
    290                 295                 300

Glu Leu Asp Arg Pro Asn Thr Glu Arg Val Thr Met Ala Gly Tyr Gly
305                 310                 315                 320

Phe Gly Leu Pro Ile Ser Arg Leu Tyr Ala Arg Tyr Phe Gly Gly Asp
                325                 330                 335

Leu Gln Ile Ile Ser Met Glu Gly Tyr Gly Thr Asp Ala Tyr Leu His
            340                 345                 350

Leu Ser Arg Leu Gly Asp Ser Glu Glu Pro Leu Pro
    355                 360

<210> SEQ ID NO 5
<211> LENGTH: 45
<212> TYPE: DNA
<213> ORGANISM: Zea mays

<400> SEQUENCE: 5
```

-continued

```
gtcacgcccg gggaattcac catggcgtcg gagccggtgg cgcgg                45

<210> SEQ ID NO 6
<211> LENGTH: 45
<212> TYPE: DNA
<213> ORGANISM: Zea mays

<400> SEQUENCE: 6
tcattactcg agctgcagct atcattacgg caagggttcc tccga                45
```